April 18, 1961 P. J. BOOY Plant Pat. 2,047
ROSE PLANT
Filed May 11, 1960
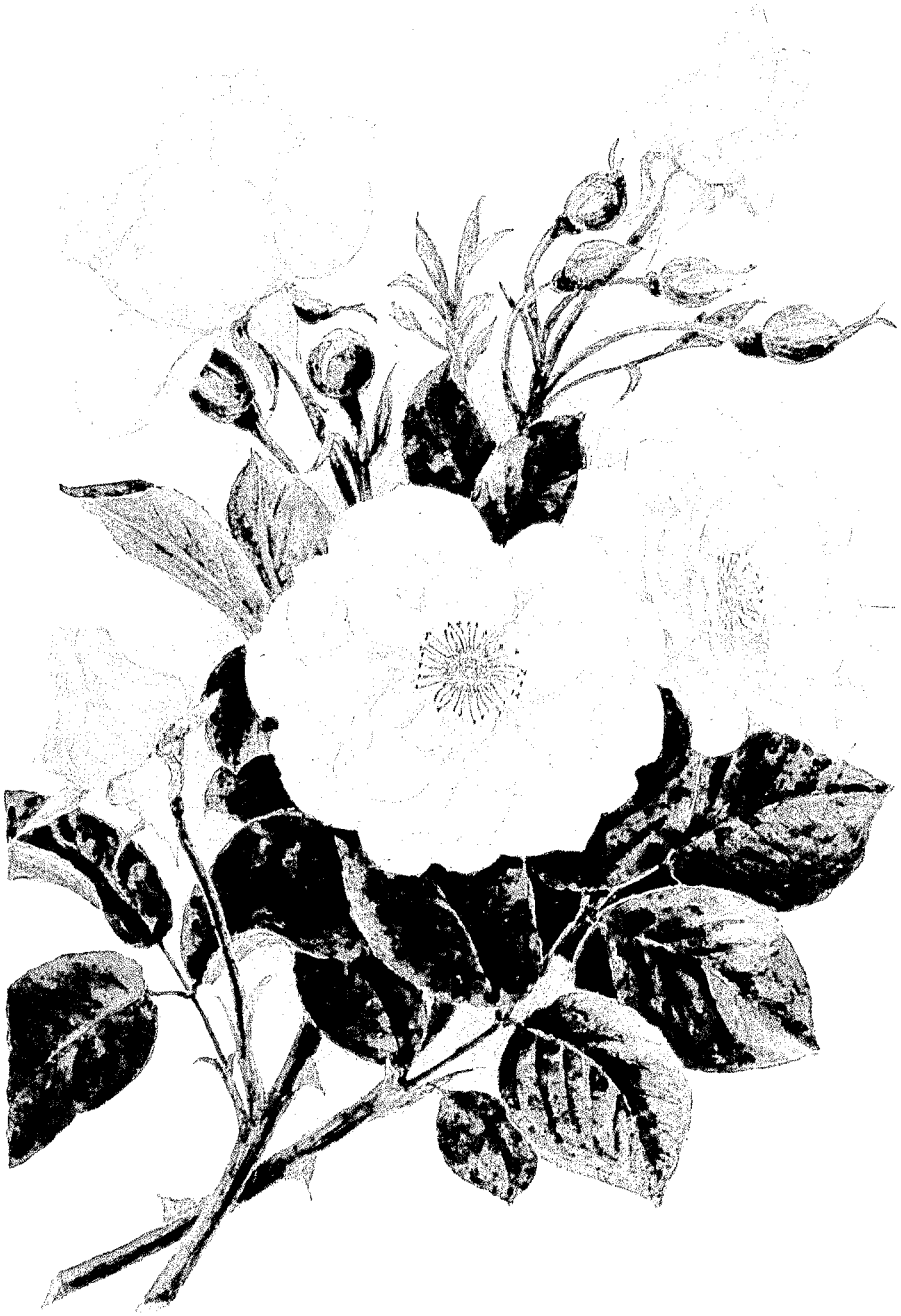
WITNESS
Addison E. Avery
INVENTOR
PETER J. BOOY
by Kummler & Snow
ATT'YS.

United States Patent Office

Plant Pat. 2,047
Patented Apr. 18, 1961

2,047

ROSE PLANT

Peter J. Booy, San Jacinto, Calif., assignor to Peter J. Booy Rose Nursery, San Jacinto, Calif., a partnership Filed May 11, 1960, Ser. No. 28,506

1 Claim. (Cl. 47—61)

My present discovery concerns a new and distinct variety of rose plant which originated as a sport of the everblooming pillar rose variety "Coral Pillar" (unpatented). My new variety of pillar rose was discovered by me in my rose gardens at San Jacinto, California and several years of asexual propagation by budding, at San Jacinto, California and at Hemet, California, under my supervision, has proved the new variety to reproduce true to form.

The new variety is similar to "Coral Pillar" in form and growing habits. However, the color of the blooms of the new variety is a rather pale yellow with tinges of pink on the petals, as distinguished from Coral Pillar which is pink. Also the new variety blooms more freely than Coral Pillar, the blooms being of medium size and borne in clusters comprising an unusually large number of buds and flowers in various stages of development.

The new plant blooms profusely and continuously, from early spring through the fall and has a vigorous, strong and upright growth reaching a height of five to eight feet with abundant foliage. Also extensive cultivation of the new plant at San Jacinto and Hemet, California has shown the plant to be highly resistant to the rose diseases prevalent in that area; namely, mildew, blackspot and cancer. Observation and testing of the new variety for disease resistance was done in the growing fields at San Jacinto and Hemet, California where the said diseases do appear to attack other rose varieties.

The accompanying illustration shows my new variety of pillar rose in full color and includes buds and flowers, in various stages of development, as well as foliage and stems, the colors shown being substantially true to the color designations hereafter set out.

The following is a detailed description of my new variety of rose plant.

Parentage: Coral Pillar (unpatented).
Classification: Pillar rose (everblooming).

*Flower*

Blooming habit: Continuous and profusely from early spring through fall.
Borne: In clusters.
Size: Medium. Diameter—3½–4 inches. Depth—1½ inches.
Shape: Cup shaped when bloom opens and form does not change materially as bloom ages.
Petalage: 25 petals, in imbricated arrangement.
*Form.*—Entire, with smooth edges.
*Color.*—Open flower—generally mimosa yellow. Outer petals—pale yellow at base to nearly white at tips with pink stripe on reverse side of some petals, pale pink tinge on inside face margins of some petals. Inside petals—yellow at base to pale yellow at tips. Petals remain on stem 4 to 8 days.
Petaloids: 4.
*Size.*—⅜" to ⅝".
*Color.*—Yellow (darker than color of petals).

Peduncle: Sturdy and upright, 3 inches long. Color—light green.
Texture: Leathery. Appearance—semi-shiny.
Fragrance: Slightly rose.
Lasting quality: On plant—good. As cut flower—good to fair.

*Bud*

Size: Medium. 1 inch in diameter, 1⅛ inches deep.
Form: Urn-shaped. Opens slowly.
Color: When sepals first divide—yellow with pink stripes. When sepals unfurl—darker yellow with pink stripes.
Sepals: Spear-shaped. Color: inside—gray green, outside—green.
Calyx: Shape—pear shaped and long. Does not split; has a smooth aspect; and is not glandular.
Peduncle: Erect—2½ inches long and not hairy. Color—light green.

*Genital organs and fruit*

Stamens:
*Anthers.*—Arranged in complete circle irregularly clustered. 4 mm. long and 110–120 in number.
*Filaments.*—5/16" long and red in color.
Pollen: Yellow in color.
Pistils: ⅜" long—78 in number.
Stigmas: Yellow in color.
Ovaries: Ordinary in character.
Fruit: Round in shape; yellow color at maturity; and fertile.

*Plant*

Form: Pillar. 5 to 8 feet in height and upright.
Growth: Strong-heavy and vigorous.
Branching: Some branching. Branches—sturdy.
Foliage: Abundant, large, elliptic-shaped, slightly serrated leaves.
*Texture.*—Leathery, glossy and smooth.
*Color.*—Upper side—dark green. Under side—light green.
*Leaflets.*—5
*Petioles.*—2½ inches in length.
*Ribs and veins.*—Not visible.
*Rachis.*—Small.
Prickles: ⅜ inch long.

The color designations, according to the Horticultural Color Chart of the British Horticultural Society and "A Dictionary of Color" by Maerz and Paul as indicated, are as follows:

| Part | Horticultural Color Chart | | Maerz and Paul | | |
|---|---|---|---|---|---|
| | Sheet | No. | Plate | Letter | No. |
| General color of bloom, "mimosa yellow". | 143 | 602 | | | |
| Outer petals, pale yellow to— | | | | | |
| Nearly white | 143 | 602/3 | | | |
| Deepest yellow at base | 143 | 602/1 to 602 | | | |
| Pale pink inside some petals | | | 1 | C | 1 |
| Pink stripe on back | | | 1 | E | 2 |
| Inner petals— | | | | | |
| Yellow at base | 143 | 602 | | | |
| Pale yellow at tip | 143 | 602/2 | | | |
| Open buds—yellow | 143 | 602/1 to 602 | | | |
| Open buds—deepest pink on outside. | | | 2 | J | 7 |
| Pistils and Stamens | | | 11 | L | 9 |
| Leaves, top side, green | | | 22 | L[1] | [1] 8 |
| Leaves, under side, light green. | | | 21 | K | 7 |
| Stems, gray green | | | 13 | L | 1 |
| Thorns (prickles) | | | 6 | C | 11 |

[1] Plus yellow.

The particularly distinctive character of my new variety of pillar rose plant resides in the unusual pale yellow color of its blooms, which runs from a deeper yellow toward the center of the bloom to a very pale yellow at the outer ends of the petals, the pink stripe on the outside of some of the petals, and the pale pink color appearing on the outer margins of the outer petals which provide a pleasing glow tc the opened flower. The variety that the plant most rearly resembles is the Coral Pillar which, however, is pink and the new variety thus adds a new color to the ever popular pillar rose class. The new variety also has the advantage of blooming more freely than its parent, Coral Pillar, which coupled with its hardy growth and disease resistant character makes the plant an attractive garden item.

Having thus described my new variety of rose plant, I claim:

A new and distinct variety of pillar rose plant, substantially as herein shown and described, characterized particularly by its more freely blooming flowers of pale yellow color tinged with pale pink on the inner surface margins of some of the outer petals, and having a pink stripe on the back side of some of the outer petals, by its strong and vigorous growth, and by its habit of blooming continuously from early spring to the end of the fall season.

No references cited.